United States Patent [19]

Wall et al.

[11] 4,079,088
[45] Mar. 14, 1978

[54] MONO-OL FROM DIOL AND IMPROVED CITRIC ACID PROCESS

[75] Inventors: Robert G. Wall, Pinole; Shigeto Suzuki, San Francisco, both of Calif.

[73] Assignee: Chevron Research Company, San Francisco, Calif.

[21] Appl. No.: 681,678

[22] Filed: Apr. 29, 1976

Related U.S. Application Data

[63] Continuation-in-part of Ser. No. 535,457, Dec. 23, 1974, abandoned.

[51] Int. Cl.² .............................................. C07C 29/00
[52] U.S. Cl. ........................... 260/642 R; 260/638 R; 260/642 E; 260/535 P
[58] Field of Search ............ 260/642 E, 642 R, 638 R

[56] References Cited

U.S. PATENT DOCUMENTS 2,997,480  8/1961  Hellin et al. .......................... 260/641

Primary Examiner—James O. Thomas, Jr.
Assistant Examiner—G. T. Breitenstein
Attorney, Agent, or Firm—D. A. Newell; John Stoner, Jr.; W. Keith Turner

[57] ABSTRACT

A process for producing 3-methyl-3-buten-1-ol from 3-methyl-2-pentene-1,5-diol which comprises heating 3-methyl-2-pentene-1,5-diol at a temperature between 200° and 450° C in the presence of isobutene.

According to a preferred embodiment, the heating step and a distillation step to separate 3-methyl-2-pentene-1,5-diol from 3-methylene-1,5-pentanediol is incorporated into a citric acid synthesis method to increase the yield of citric acid from isobutene plus formaldehyde.

4 Claims, 1 Drawing Figure

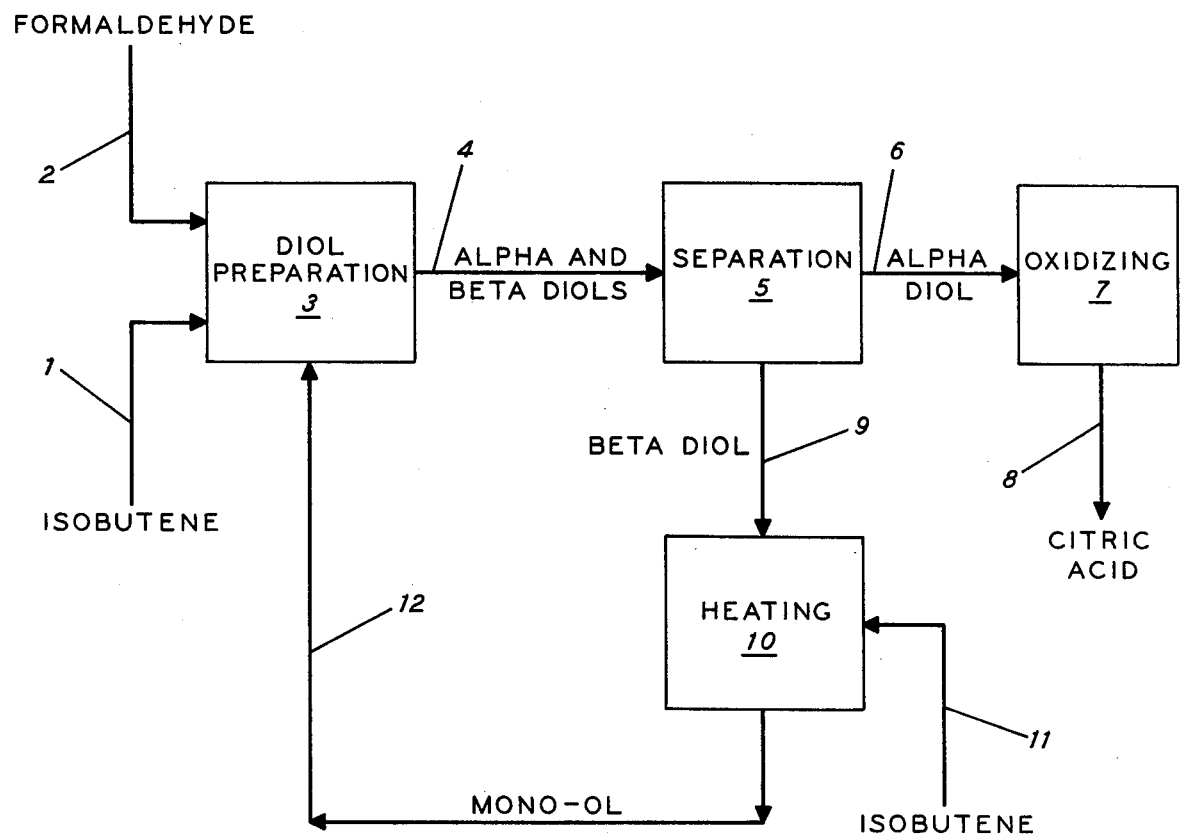

MONO-OL FROM DIOL AND IMPROVED CITRIC ACID PROCESS

CROSS-REFERENCE TO RELATED APPLICATION

This application is a continuation-in-part of U.S. application Ser. No. 535,457, filed Dec. 23, 1974, now abandoned.

BACKGROUND OF THE INVENTION

The present invention relates to the production of an alkene mono-ol and also to the synthesis of citric acid.

Production of alkene mono-ols is disclosed in U.S. Pat. No. 3,574,773. Thus, according to Example 4 of U.S. Pat. No. 3,574,773, formaldehyde is reacted with isobutene to obtain monool.

U.S. Pat. No. 3,692,848 discloses the production of alkenediols from mono-ol by reaction of the mono-ol with formaldehyde.

Commonly assigned patent applications Ser. Nos. 379,511 and 427,176 disclose the preparation of alkenediols, e.g., 3-methylene-1,5-pentanediol (alpha-diol) and 3-methyl-2-pentene-1,5-diol (beta-diol) by reaction of isobutene with formaldehyde. Commonly assigned Ser. No. 491,987 discloses the conversion of alpha-diol to citric acid in an oxidation process. The disclosures of these three applications are incorporated herein by reference, particularly in that they relate to preparation of alpha- and beta-diols, and to conversion of alpha-diol to citric acid.

In view of the present invention, we have also located an article by G. Ohloff in Chem. Ber., Vol. 93, p. 2673 (1960) which discloses the thermal (temperature = 350° C) splitting off of formaldehyde from a cyclic beta-hydroxy olefin. Also, Smith and Yates in J. Chem. Soc. (1965), p. 7242, disclose pyrolysis of but-3-en-1-ol (370° C) to obtain propene and formaldehyde and the pyrolysis of pent-4-en-2-ol to produce propene and acetaldehyde.

The thermal condensation of formaldehyde with an olefin is disclosed in F. Asinger's book *Monoolefins — Chemistry and Technology*, Pergamon Press (1968), p. 719.

SUMMARY OF THE INVENTION

According to the present invention, a process is provided for producing 3-methyl-3-buten-1-ol from 3-methyl-2-pentene-1,5-diol which comprises heating 3-methyl-2-pentene-1,5-diol at a temperature between 200° and 450° C in the presence of isobutene.

The conversion of the beta-diol in the process of the present invention can be largely summarized by the following equation:

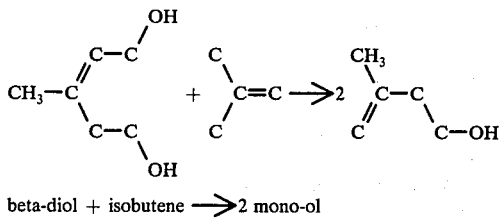

beta-diol + isobutene ⟶ 2 mono-ol

The term "beta-diol" is thus used herein to describe cis and/or trans 3-methyl-2-pentene-1,5-diol, whereas "alpha-diol" is used to describe 3-methylene-1,5-pentanediol, and "mono-ol" is used to describe 3-methyl-3-buten-1-ol.

Among other factors, the present invention is based on our finding that the beta-diol can be converted in good yield to mono-ol and also our conception and finding that the method can be advantageously integrated, as defined hereinbelow, into a synthetic process for producing citric acid.

We have found that a mixture of alpha- and beta-diol can be practically separated by distillation into a beta-diol-rich fraction and an alpha-diol-rich fraction. The alpha-diol can be converted to citric acid by oxidation as described in Ser. No. 491,987. The alpha- and beta-diol mixture can be generated in the first instance by various means, for example from isobutene and formaldehyde, as described in Ser. Nos. 379,511 and 427,176.

According to a preferred embodiment of our invention, a process is provided for improving the yield of citric acid from a citric acid synthesis method wherein citric acid is obtained by: (1) reacting isobutene and/or 3-methyl-3-buten-1-ol, i.e., mono-ol, with formaldehyde to obtain a mixture of 3-methylene-1,5-pentanediol and 3-methyl-2-pentene-1,5-diol, i.e., alpha- and beta-diol; and (2) oxidizing the 3-methylene-1,5-pentanediol to citric acid, which process comprises:

(a) reacting isobutene or 3-methyl-3-buten-1-ol (mono-ol) with formaldehyde to obtain a mixture of 3-methylene-1,5-pentanediol and 3-methyl-2-pentene-1,5-diol (alpha- and beta-diols, respectively);

(b) separating the beta-diol from the alpha/beta-diol mixture, (c) heating the beta-diol to a temperature between 200° and 450° C in the presence of isobutene to obtain mono-ol;

(d) recycling the mono-ol from step (c) to step (a); and (e) feeding the alpha-diol from step (b) to the oxidation step of the citric acid synthesis method.

Thus, in this preferred embodiment, mono-ol is generated from beta-diol and the thus-obtained mono-ol is reacted with formaldehyde to generate additional alpha-diol. The alpha-diol is advantageously converted to citric acid by oxidation.

Preferred temperature for use in the process of the present invention is between about 200° and 450° C, more preferably between 250° and 440° C.

According to an alternate embodiment, a process is provided for the conversion of beta-diol to a mixture of formaldehyde and 3-methyl-3-buten-1-ol which comprises heating the beta-diol at a temperature in the range 350°–450° C and without the addition of isobutene being required. According to another alternate, the beta-diol is converted to a mixture of formaldehyde and isobutene by heating the beta-diol at a somewhat higher temperature, for example about 400°–500° C, preferably 450°–500° C. These alternates can be integrated, together with distillation to separate beta-diol from alpha-diol, into a method for synthesizing citric acid, as described above, and wherein the 3-methyl-3-buten-1-ol and formaldehyde and isobutene obtained by the heating are recycled at least in part to the first step of the citric acid synthesis process wherein the alpha- and beta-diol are produced.

Referring again more particularly to the present invention wherein at least one of the steps of the invention embraces the heating of beta-diol in the presence of added isobutene, preferred amounts of added isobutene are between 20% and 80% of the combined beta-diol and isobutene, and more preferably between 50 and 80 weight percent.

Preferably the pressure used in the heating of the beta-diol to obtain the mono-ol is between about 10 and 5000 psig, and more preferably between about 1000 and 3000 psig.

As indicated previously, the present invention preferably embraces a step for separation of beta-diol from alpha-diol by distillation to obtain a beta-diol-rich fraction and an alpha-diol-rich fraction. The term "rich" is used to refer to a fraction containing at least 50 weight percent beta-diol and more preferably at least 80 weight percent beta-diol; and with respect to alpha-diol at least 60 weight percent alpha-diol and more preferably at least 90 weight percent alpha-diol. Some of the constituents which may be present in the respective beta-diol-rich fraction and alpha-diol-rich fraction resulting from the distillation of an alpha/beta-diol mixture, wherein the mixture is generated by reaction of isobutene or mono-ol with formaldehyde, are unidentified by-products from the olefinformaldehyde condensation reaction.

BRIEF DESCRIPTION OF THE DRAWING

The drawing is a schematic process flow diagram illustrating a preferred embodiment of the present invention in simplified form. Isobutene and formaldehyde are fed to diol preparation zone 3 wherein they are reacted to make a mixture of alpha- and beta-diols. The alpha- and beta-diols are fed via line 4 to separation zone 5, which preferably comprises a distillation unit for separating alpha- and beta-diol-rich fractions. The alpha-diol material is fed via line 6 to oxidation zone 7 for oxidation to citric acid, preferably using nitric acid and nitrogen dioxide. After suitable separation, the citric acid is withdrawn via line 8.

Beta-diol is withdrawn from separation zone 5 and is fed as indicated by line 9 to heating zone 10. In heating zone 10 the beta-diol is heated to a temperature between about 250° and 500° C, preferably in the presence of added isobutene introduced via line 11, to obtain mono-ol and/or formaldehyde and isobutene from the beta-diol, and the thus-obtained materials are recycled via line 12 to diol preparation zone 3 for the production of further alpha-diol. The heating zone 10 can include or be integrated with a separation zone so that separated, unconverted, beta-diol from the heating step can be recycled, separated alpha-diol can be fed to zone 7, and separated mono-ol passed via line 12 to diol preparation zone 3.

EXAMPLES

EXAMPLE 1

A 1.1-g portion of beta-diol (containing 14.3% alpha-isomer) was pyrolyzed by passing the diol at an LHSV (liquid hourly space velocity) of 0.55 through an externally heated stainless steel tube having an ID of 3/16 inch and a length of 8 inches. Carrier nitrogen flow rate was 2-3 cc/min. The temperature was maintained at 390° C. The effluent of 0.87 g was collected in a dry-ice trap. The effluent consisted essentially of only 4 products: alpha- and beta-diols (94%), mono-ol (4%) and formaldehyde (2%). The analyses herein are by weight percent unless indicated otherwise.

EXAMPLE 2

In a manner similar to Example 1, 0.77 g of beta-diol was pyrolyzed at 440° C and an LHSV of 1.4. The effluent trapped, 0.60 g, consisted of alpha- and beta-diols (83%), mono-ol (9%) and formaldehyde (balance).

EXAMPLE 3

In a manner similar to Example 1, beta-diol (containing 25% in alpha-diol), 1.15 g, was pyrolyzed at an LHSV of 1.1 and at 495° C. The effluent trapped (±0.7 g) consisted mainly of isobutene, formaldehyde, small amounts of water and diols (less than 8% of the effluent).

EXAMPLE 4

In a manner similar to Example 1, the beta-diol used in Example 3 (1.44 g) was pyrolyzed at an LHSV of 1.4 and at 475° C. The effluent trapped (±0.9 g) consisted of mainly isobutylene, formaldehyde and a small amount of water.

The above examples 1-4 show that beta-diol can be converted to mono-ol by heating at a temperature between 200°-450° C. Examples 1 and 2 show that at relatively lower temperature little or no isobutene is produced, whereas Examples 3 and 4 show that isobutene is produced from the beta-diol at temperatures between 450° and 500° C.

EXAMPLE 5

A 2-g sample containing 33% 3-methylene-1,5-pentanediol (alpha-diol) and 55% 3-methyl-2-pentene-1,5-diol (beta-diol) was sealed into a microbomb of approximately 15 ml capacity. The mixture was heated and shaken at 260° C for 1 hour. A liquid product weighing 1.84 g was obtained which analyzed to be 7.1% alpha-diol, 11.03% beta-diol and 5.74% 3-methyl-3-buten-1-ol (mono-ol). The conversion of diol was 80% and the yield of mono-ol was 10% (by mol).

EXAMPLE 6

A 2-g sample of the same diol mixture was placed in a sealed microbomb with 2 g isobutene. After 1 hour at 260° C, 1.96 g of liquid product was obtained. The product analyzed to be 12.2% alpha-diol, 23.5% beta-diol and 12.7% mono-ol. The diol conversion was 60% and the yield of mono-ol was 32% (by mol).

Thus, Example 6 compared to Example 5 shows increased production of mono-ol from beta-diol when the heating of the beta-diol is carried out in the presence of isobutene, particularly in the presence of isobutene added to the reaction zone.

We claim:

1. A process for producing 3-methyl-3-buten-1-ol from 3-methyl-2-pentene-1,5-diol which comprises feeding 3-methyl-2-pentene-1,5-diol and isobutene to a reaction zone and therein heating said diol and the isobutene at a temperature between 200° and 450° C, and wherein the reaction is carried out at a pressure between 10 and 5000 psig and the amount of isobutene fed is 20 to 80 weight percent based on the combined diol and isobutene.

2. A process in accordance with claim 1 wherein the amount of isobutene is between 20 and 80 weight percent based on 3-methyl-2-pentene-1,5-diol plus isobutene.

3. A process in accordance with claim 1 wherein the temperature is between 250° and 440° C.

4. A process in accordance with claim 1 wherein the 3-methyl-2-pentene-1,5-diol is obtained from a mixture of 3-methylene-1,5-pentanediol and 3-methyl-2-pentene-1,5-diol by separating a 3-methyl-2-pentene-1,5-diol-rich fraction from the mixture by distillation.

* * * * *